(12) United States Patent
Berger et al.

(10) Patent No.: US 6,504,026 B2
(45) Date of Patent: Jan. 7, 2003

(54) PROCESS FOR PRODUCTION OF CEFTIOFUR

(75) Inventors: Andreas Berger, Kufstein (AT); Martin Decristoforo, Kramsach (AT); Johannes Ludescher, Breitenbach (AT); Herbert Schleich, Kundl (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 09/989,557

(22) Filed: Nov. 20, 2001

(65) Prior Publication Data

US 2002/0082248 A1 Jun. 27, 2002

Related U.S. Application Data

(60) Provisional application No. 60/252,707, filed on Nov. 22, 2000.

(51) Int. Cl.[7] ............................................. C07D 501/36
(52) U.S. Cl. ........................................ 540/227; 540/220
(58) Field of Search ........................ 514/206; 540/220, 540/227

(56) References Cited

U.S. PATENT DOCUMENTS

| | | | |
|---|---|---|---|
| 4,877,782 A | * 10/1989 | Cazers et al. | 514/186 |
| 4,902,683 A | * 2/1990 | Amin et al. | 514/206 |
| 4,937,330 A | * 6/1990 | Sacks et al. | 540/227 |
| 5,403,929 A | 4/1995 | Hsieh | |
| 5,491,259 A | 2/1996 | Grierson et al. | |
| 6,100,393 A | 8/2000 | Lopez Ortiz et al. | |
| 2002/0028931 A1 | * 3/2002 | Dandala | 540/227 |

FOREIGN PATENT DOCUMENTS

| | | |
|---|---|---|
| EP | 476 875 A2 | 3/1992 |
| EP | 822 195 B1 | 2/1998 |
| WO | WO 87/01117 | 2/1987 |
| WO | WO 99/53015 | 10/1999 |
| WO | WO 00/12200 | 3/2000 |

OTHER PUBLICATIONS

Derwent Abstract WPI AN 1999–012142 (Abstract of JP 04–338332 A published Nov. 25, 1992).
Derwent Abstract WPI AN 1999–585823 (Abstract of JP 11–255653 A published Sep. 21, 1999).
Derwent Abstract 2000–225324/20 Mar. 2, 2000 (DE 19839209–A1)—equivalent of WO 00/1220.
Abstract of Redondo, Jorge et al., Chem. Inc. (Duesseldorf) vol. 111, No. 9, pp. 66,68, (1988).
Abstract of Bryk, M.T. et al., Khim. Tekhnol. Vody vol. 17, No. 4, pp. 375–397 (1995).
Abstract of Zhang, Wei et al., Zhongguo Kangshengsu Zazhi, vol. 24, No. 2, pp. 99–101 (1999).
Abstract of Wu, Lihua et al., Mo Kexue Yu Jishu, vol. 17, No. 5, pp. 11–15 (1997).
Abstract of Wang, Xiaolin et al., Nanjing Huagong Daxue Xueban, vol. 22, No. 3, pp. 68–71 (2000).
Abstract of Wang, Xiaolin et al., Mo Kexue Yu Jishu, vol. 10, No. 1, pp. 29–36 (2000).
Derwent Abstract 86–216136/33, Jul. 5, 1986 (J6 1148–180–A).
Derwent Abstract 93–299638/38, Aug. 24, 1993 (JP 05213963–A).
Derwent Abstract 90–266216/35, Jul. 24, 1990 (JO 2188–586–A).

* cited by examiner

*Primary Examiner*—Mark L. Berch
(74) *Attorney, Agent, or Firm*—Peter J. Waibel; Diane E. Furman

(57) ABSTRACT

Process for preparing ceftiofur having formula I:

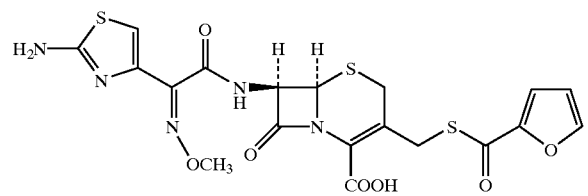

in the form of the sodium salt.

7 Claims, No Drawings

PROCESS FOR PRODUCTION OF CEFTIOFUR

This application claims the benefit of provisional application No. 60/252,707 filed Nov. 22, 2000.

The present invention relates to organic compounds, such as cephalosporins, more specifically to ceftiofur of formula

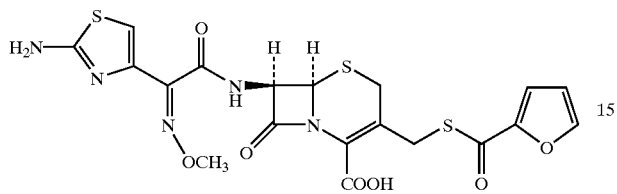

I which is {6R-[6α,7β(Z)]}-7-{[(2-amino-4-thiazolyl) (methoxyimino)acetyl]amino}-3-{[(2-furanylcarbonyl)-thio]methyl }-8-oxo-5-thia-1-azabicyclo[4.2.0]oct-2-ene-2-carboxylic acid, e.g. described in The Merck Index, 12th edition, item 1999. Ceftiofur is known as a pharmaceutically active compound, e.g. useful as an antibiotic, such as an antibacterial agent, e.g. used in veterinary medicine, e.g. in the form of a salt with sodium and in the form of a salt with hydrochloric acid. Processes for the production of ceftiofur in free form, in the form of a salt with hydrochloric acid or hydrobromic acid or in the form of a sodium salt are known. Ceftiofur in the form of a sodium salt is chemically not very stable and is difficult to purify. E.g. for purification ceftiofur may be converted into a crystalline salt with hydrochloric acid or hydrobromic acid which may be used as a starting material for the production of ceftiofur in the form of a sodium salt. E.g. a known production process of ceftiofur in the form of a sodium salt comprises the following steps a) treating ceftiofur in the form of a salt with hydrochloric or hydrobromic acid in aqueous organic solvent with polyvinylpyridine, which polyvinylpyridine is activated by treatment with aqueous hydrochloric acid, rinsing with water, treatment with 10% sodium hydroxide solution, rinsing with water and tetrahydrofurane and drying, to obtain a solution comprising ceftiofur, b) filtering the solution obtained in step a) to remove the polyvinylpyrrolidone;

c) treating the filtrate obtained in step b) with 2-ethydhexanoic acid in the form of a sodium salt to obtain ceftiofur in the form of a sodium salt, and d) isolating ceftiofur in the form of a sodium salt by precipitation from an aqueous organic solvent.

Ceftiofur in the form of a sodium salt may be obtained in amorphous form.

We have now surprisingly found a process for the production of pure ceftiofur in the form of a sodium salt starting from ceftiofur in the form of a salt with hydrochloric acid or hydrobromic acid, wherein the use of activated polyvinylpyrrolidone may be avoided.

In one aspect the present invention provides a process for the production of ceftiofur of formula I in the form of a sodium salt comprising the steps a) treating a compound of formula I in the form of a salt with hydrochloric acid or hydrobromic acid with a basic sodium source, erg. sodium hydroxide, sodium carbonate, sodium bicarbonate; in aqueous solvent; e.g. in water; to obtain a compound of formula I in the form of a sodium salt beside sodium chloride or sodium bromide in aqueous solvent, e.g. water;

b) separating a compound of formula I in the form of a sodium salt from sodium chloride or sodium bromide in aqueous solvent obtained in step a) by use of an appropriate membrane separation system e.g. comprising a membrane which is appropriate for separation of sodium chloride or sodium bromide from a compound of formula I in the form of a sodium salt in aqueous solution, e.g. selected from a polyamide thinfilm composite on a polysulfone carrier or a ceramic membrane; and comprising means for removal of a solution of sodium chloride or sodium bromide from the system and for adding fresh water to the system; and c) isolating a compound of formula I in the form of a sodium salt obtained in step b), e.g. by lyophilisation or spray drying, e.g. optionally after concentration of the solution obtained in step b).

A process according to the present invention may be carried out as follows: A compound of formula I in the form of a salt with hydrochloric acid or hydrobromic acid may be suspended or dissolved in aqueous solvent, e.g. including water or a mixture of water and an appropriate organic solvent, preferably water. It is one advantage of the present invention that organic solvent may be avoided. The mixture obtained is treated with an appropriate basic sodium source, e.g. including sodium hydroxide, sodium carbonate, sodium bicarbonate. The basic sodium source may be in solid form or in solution, e.g. in aqueous solution. A pH of 5 to 9, preferably of 5 to 7.5, is adjusted in the mixture obtained. Treatment with the basic sodium source is carried out at appropriate temperatures, e.g. including temperatures of 0° C. to about 30° C., preferably of 0° C. to 5° C. A solution is obtained comprising a compound of formula I in the form of a sodium salt beside sodium chloride or sodium bromide, which optionally may be treated with charcoal and/or an adsorber resin, e.g. for de-colorizing or clear filtration. The solution obtained is subjected to a membrane separation system comprising a membrane which is appropriate for separation of sodium chloride or sodium bromide from a compound of formula I in the form of a sodium salt in aqueous solution and comprising means for removal of a solution of sodium chloride or sodium bromide from the system and for adding fresh water to the system. Appropriate membranes include nanofiltration membranes having a cut-off of ca. 100 to 500 Dalton, a retention of MgSO4 of over 90%; e.g. and a retention of sodium chloride of below 80%. Such membranes are known and commercially available, e.g. a including polyamide thinfilm composite on a polysulfone carrier, such as the membranes Nanomax 50® of the firm Millipore, NF 45® or NF 70® of the firm Danish Separation Systems, SR-1®, SR-2® or MPF44® of the firm Koch, or other comparable membranes of the firms Celgard, Nitto Denko or PCI; and including ceramic membranes, e.g. ceramic membranes comprising separating layers from titanium or zirconium oxides and an aluminium oxide carrier material. The membrane separation system is run as appropriate, e.g. a separated solution of sodium chloride or sodium bromide is removed from the system and fresh water is added. Separation is run at appropriate temperatures e.g. including temperatures of 0° C. to about 30° C., preferably of 0° C. to 5° C. The concentration of the solution of a compound of formula I and sodium chloride or sodium bromide is not critical but separation is faster in a high concentrated solution compared with a low concentrated solution. Convenient concentrations include concentrations of a compound of formula I in the form of a sodium salt and of sodium chloride or bromide in water of 1% to 30%, preferably of 10% to 15%. A solution of a compound of formula I in the form of a sodium salt is obtained which is substantially free of sodium chloride or sodium bromide. A compound of formula I in the form of a sodium salt may be isolated from the solution obtained as appropriate, e.g. according to a method as conventional, e.g. including direct lyophilisation or spray drying, or, the solution obtained may be concentrated as appropriate e.g. according to a method as conventional, e.g. including solvent evaporation, reversed osmosis, and the concentrated solution may be subjected to lyophilisation or spray drying.

Before isolation of a compound of formula I in the form of a sodium salt a buffer may be added to the solution, e.g. including primary or tertiary sodium or potassium phosphate-buffers.

A compound of formula I in the form of a sodium salt in solid, amorphous form may be obtained, substantially free of sodium chloride or sodium bromide, e.g. containing 0.05% and less of sodium chloride or sodium bromide.

A compound of formula I in the form of a sodium salt in solid, amorphous form obtained according to the present invention is useful in the production of pharmaceutical compositions comprising ceftiofur as a pharmaceutically active compound beside pharmaceutically acceptable excipients, e.g. in sterile or non-sterile form.

In another aspect the present invention provides the use of a compound of formula I in the form of a sodium salt, e.g. in solid, amorphous form, obtained according to the present invention in the production of a pharmaceutical composition comprising an effective amount of ceftiofur as a pharmaceutically active compound beside pharmaceutically acceptable excipients.

A pharmaceutical composition comprising ceftiofur as a pharmaceutically active compound beside pharmaceutically acceptable excipients e.g. in sterile or non-sterile form, may be produced as appropriate, e.g. according to a process as conventional, using a compound of formula I in the form of a sodium salt in solid, amorphous form obtained according to the present invention. Effective amounts of ceftiofur in a pharmaceutical composition are known.

In another aspect the present invention provides the use of a compound of formula I in the form of a sodium salt, e.g. in solid, amorphous form, obtained according to the present invention in sterile form as an antibiotic.

EXAMPLE 500 g of ceftiofur in the form of a salt with hydrochloric acid in 10 l of water are stirred at a temperature of 5 to 10° C. To the mixture obtained an aqueous 5% sodium hydroxide solution is added and a pH of 7.5 is adjusted at a temperature which does not exceed 5° C. The mixture obtained is filtrated, treated with active charcoal and the charcoal is filtrated off. The solution obtained is subjected to a membrane separation system comprising a membrane which is a polyamide thinfilm composite on a polysulfone carrier (NANOMAX 50®, Millipore-membrane) and comprising means for removal of a solution of sodium chloride from the system and for adding fresh water to the system. A back pressure of 30 bar is adjusted. A continuous flow of a solution comprising sodium chloride in isotonic concentration through the membrane is obtained and ceftiofur in the form of a sodium salt is substantially complete retained by the membrane. The volume of the solution of ceftiofur in the form of a sodium salt is kept approximately constant by addition of fresh water to the system. After a six-fold exchange of the volume of water ceftiofur in the form of a sodium salt is practically free of sodium chloride. The solution comprising ceftifur in the form of a sodium salt is concentrated to obtain a concentration of 10% to 30% (w/w) and the concentrate obtained is subjected to lyophilisation. Ceftiofur in the form of a sodium salt in amorphous form is obtained. Yield: >90%; content chloride: <0.05%.

What is claimed is:

1. A process for the production of ceftiofur of formula

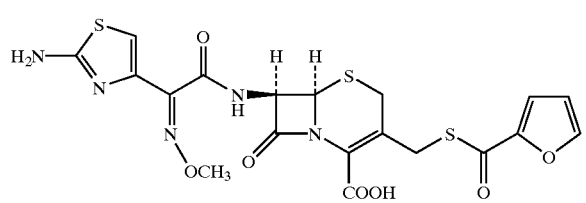

I in the form of a sodium salt comprising the steps a) treating a compound of formula I in the form of a salt with hydrochloric acid or hydrobromic acid with a basic sodium source in aqueous solvent to obtain a compound of formula I in the form of a sodium salt along with sodium chloride or sodium bromide in aqueous solvent;

b) separating a compound of formula I in the form of a sodium salt from sodium chloride or sodium bromide in aqueous solvent obtained in step a) by filtering through a membrane separation system; and c) isolating a compound of formula I in the form of a sodium salt obtained in step b).

2. A process according to claim 1 wherein a basic sodium source is selected from sodium hydroxide, sodium carbonate or sodium bicarbonate.

3. A process according to claim 1 wherein the aqueous solvent is water.

4. A process according to claim 1 wherein the membrane separation system comprises a membrane which is appropriate for separation of sodium chloride or sodium bromide from a compound of formula I in the form of a sodium salt in aqueous solution and comprises means for removal of a solution of sodium chloride or sodium bromide from the system and for adding fresh water to the system.

5. A process according to claim 1 wherein a compound of formula I in the form of a sodium salt is isolated by lyophilisation or spray drying.

6. A process according to claim 1 wherein a compound of formula I in the form of a sodium salt is isolated after concentration of the solution obtained in step b).

7. A process according to claim 1 wherein the membrane is selected from a polyamide thinfilm composite on a polysulfone carrier or a ceramic membrane.

* * * * *